United States Patent
Stuiver et al.

(10) Patent No.: US 6,987,179 B1
(45) Date of Patent: Jan. 17, 2006

(54) CONSTITUTIVE PLANT PROMOTERS

(75) Inventors: Maarten Hendrik Stuiver, Oegstgeest (NL); Floor Hendrik Sijbolts, Almere (NL)

(73) Assignee: Syngenta Mogen B.V., Lieden (NL)

( * ) Notice: Subject to any disclaimer, the term of this patent is extended or adjusted under 35 U.S.C. 154(b) by 0 days.

(21) Appl. No.: 09/581,331

(22) PCT Filed: Dec. 10, 1998

(86) PCT No.: PCT/EP98/08162

§ 371 (c)(1),
(2), (4) Date: Jul. 21, 2000

(87) PCT Pub. No.: WO99/31258

PCT Pub. Date: Jun. 24, 1999

(30) Foreign Application Priority Data

Dec. 12, 1997 (EP) .................................. 97203912

(51) Int. Cl.
*C12N 15/82* (2006.01)

(52) U.S. Cl. .................................. 536/24.1; 435/320.1

(58) Field of Classification Search ............... 536/23.1, 536/24.1; 435/320.1, 419
See application file for complete search history.

(56) References Cited

U.S. PATENT DOCUMENTS

| 5,097,025 A | 3/1992 | Benfy et al. .................. 536/27 |
| 5,106,739 A | 4/1992 | Comai et al. ............. 435/172.3 |

FOREIGN PATENT DOCUMENTS

| EP | 0 559 603 A2 | | 9/1993 |
| WO | WO 92/18625 | | 10/1992 |
| WO | WO 94/12015 | | 6/1994 |
| WO | WO 95/14098 | * | 5/1995 |
| WO | WO 97/20056 | | 6/1997 |

OTHER PUBLICATIONS

Fiedler et al 1993, Plant Molecular Biology 22: 660-679.*
Puente et al 1996, The EMBO Journal 15(14): 3732-3743.*
Kononowicz, H. et al., The Plant Cell, vol. 4, No. 1, pp. 17-27, Jan. 1992.

* cited by examiner

*Primary Examiner*—David H Kruse
(74) *Attorney, Agent, or Firm*—Michael Yates

(57) ABSTRACT

The invention describes new promoters built from elements from a set of promoters which have a complementary expression pattern.

8 Claims, 6 Drawing Sheets

US 6,987,179 B1

CONSTITUTIVE PLANT PROMOTERS

FIELD OF THE INVENTION

The invention is directed to new plant promoters, more specifically those promoters which can be produced by assembling parts of promoters which have a complementary specificity.

BACKGROUND ART

Genetic engineering of plants has become possible by virtue of two discoveries: first of all the possibility of transformation of heterologous genetic material to the plant cell (most efficiently done by the bacterium *Agrobacterium tumefaciens* or related strains) and secondly by the existence of plant promoters which are able to drive the expression of said heterologous genetic material.

A typical plant promoter consists of specific elements. A basis is formed by the minimal promoter element, which enables transcription initiation, often accompanied by a sequence, also denominated as the TATA-box, which serves as a binding place for transcription initiation factors. In most promoters; the presence of this TATA-box is important for proper transcription initiation. It is typically located 35 to 25 basepairs (bp) upstream of the transcription initiation site. Another part of the promoter consists of elements which are able to interact with DNA-binding proteins. Known are G-box binding elements which are based on the hexanucleotide CACGTG motif. These elements have been shown to be able to interact with bZIP DNA-binding proteins which bind as dimers (Johnson & McKnight, Ann. Rev. Biochem, 58, 799–839, 1989). Other G-box related motifs, such as the Iwt and PA motifs have been described (WO 94/12015).

These motifs have been shown to be involved in tissue-specific promoter expression in plants. For instance, presence of Iwt tetramers confer embryo-specific expression, while PA tetramers confer high level root expression, low-level leaf expression and no seed expression.

Similarly, GT-1 like binding sites (grouped on basis of a moderate consensus sequence $GGT^A/_TA$) are described. Such a binding site is found far upstream the promoter region of the *Arabidopsis plastocyanin* promoter and seems to be involved in activation of transcription during light periods (Fisscher, U. et al., Plant Mol. Biol. 26, 873–886, 1994).

Another sequence-related phenomenon which is found often in plant promoters is the presence of sequences which enable the formation of Z-DNA. Z-DNA is DNA folded in a left-handed helix which is caused by repeats of dinucleotides GC or AC. It is believed that folding in a Z-form influences the availability of the DNA for approach by RNA polymerase molecules, thus inhibiting the transcription rate.

One of the earliest and most important inventions in the field of plant protein expression is the use of (plant) viral and *Agrobacterium*-derived promoters that provide a powerful and constitutive expression of heterologous genes in transgenic plants. Several of these promoters have been used very intensively in plant genetic research and still are the promoter of choice for rapid, simple and low-risk expression studies. The most famous are the 35S and 19S promoter from Cauliflower Mosaic Virus (CaMV), which was already found to be practically useful in 1984 (EP 0 131 623), the promoters which can be found in the *Agrobacterium* T-DNA, like the nopaline synthase (nos), mannopine synthase (mas) and octopine synthase (ocs) promoters (EP 0 122 791, EP 0 126 546, EP 0 145 338). A plant-derived promoter with similar characteristics is the ubiquitin promoter (EP 0 342 926).

In time, several attempts have been made to increase the level of expression of these promoters. Examples for this are the double enhanced 35S promoter (U.S. Pat. No. 5,164,316) and, more recently, the superpromoter, which couples parts of the *Agrobacterium* promoters (EP 729 514).

However, in many cases these promoters do not fulfill the criteria of an ideal promoter. All promoters described above show a clear pattern of organ- or developmental-specific expression, and frequently the pattern of expression found with these promoters is not ideal for some applications. Especially for biotechnological applications like the engineering of fungal and insect resistance, which require expression both in the right location as well as in the right timeframe of plant development there is a need for new constitutive promoters which are able to give a high level of transgene expression at exactly the right time and place.

SUMMARY OF THE INVENTION

The invention provides for novel plant promoters, characterized in that they comprise 1) a minimal promoter and 2) transcription-activating elements from a set of promoters, which elements direct a complementary pattern and level of transcription in a plant.

More specifically, this plant promoter is a constitutive promoter in which each of the transcription-activating elements do not exhibit an absolute tissue-specificity, but mediate transcriptional activation in most plant parts at a level of $\geq 1\%$ of the level reached in the part of the plant in which transcription is most active. An example of such promoter pairs is a set of promoters in which one is most active in green parts of the plant, while the other promoter is most active in underground parts of the plant. More specifically the new promoter is a combination of the ferredoxin and the RolD promoter. Preferably in this construct the minimal promoter element is derived from the ferredoxin promoter and the ferredoxin promoter is derived from *Arabidopsis thaliana*. The rolD promoter is derived from *Agrobacterium rhizogenes*.

Also part of the invention is a plant promoter which is a combination of the plastocyanin and the S-adenosyl-methionine-1 promoter, whereby preferably the minimal promoter element is derived from the S-adenosyl-methionine-1 promoter and both the plastocyanin promoter and the S-adenosyl-methionine-1 promoter are derived from *Arabidopsis thaliana*.

Further part of the invention are chimaeric gene constructs for the expression of genes in plants comprising the above disclosed promoters.

DETAILED DESCRIPTION OF THE INVENTION

Figure 1:
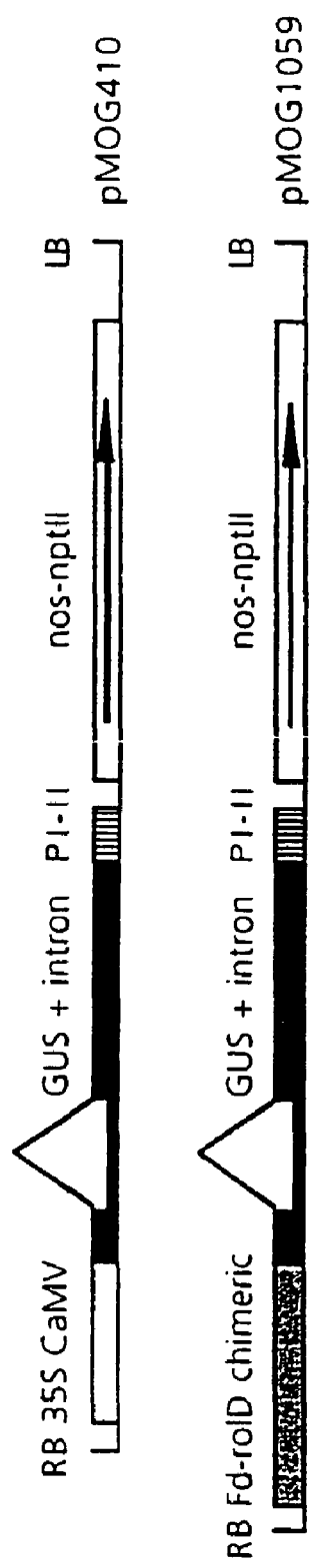
FIG. 1: Schematic representation of pMOG410 and pMOG1059

For the purpose of this specification the following definitions are valid:

A promoter consists of an RNA polymerase binding site on the DNA, forming a functional transcription initiation start site. A promoter usually consists of at least a TATA box and possibly of other sequences surrounding the transcription initiation site (initiator) and can either be used isolated (minimal promoter) or linked to binding sites of transcription-activating elements, silencers or enhancers that may enhance or reduce transcription initiation rates, and which may function respective of developmental stage, or external or internal stimuli.

The initiation site is the position surrounding the first nucleotide which is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

A minimal promoter is a promoter consisting only of all basal elements needed for transcription initiation, such as a TATA-box and/or initiator.

An enhancer is a DNA-element which, when present in the neighbourhood of a promoter is able to increase the transcription initiation rate.

A promoter is constitutive when it is able to express the gene that it controls in all or nearly all of the plant tissues during all or nearly all developmental stages of the plant.

Specific expression is the expression of gene products which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The expression pattern of a promoter (with or without enhancer) is the pattern of expression levels which shows where in the plant and in what developmental stage transcription is initiated by said promoter.

Expression patterns of a set of promoters are said to be complementary when the expression pattern of one promoter shows little overlap with the expression pattern of the other promoter.

The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore the steady state level is the product of synthesis rates and degradation rates. The rate of degradation can however be considered to proceed at a fixed rate when the transcribed sequences are identical, and thus this value can serve as a measure of synthesis rates. When promoters are compared in this way techniques available to those skilled in the art are hybridisation S1-RNAse analysis, Northern blots and competitive RT-PCR. This list of techniques in no way represents all available techniques, but rather describes commonly used procedures used to analyse transcription activity and expression levels of mRNA.

One of the technical difficulties encountered in such an analysis is that the qualitatively best results can only be obtained by fusing transcriptional activating parts to the reporter RNA molecule, in such a way that only reporter sequences are transcribed. This requires the exact determination of the RNA synthesis start, and joining at that point the sequences of the reporter mRNA.

This is important for a number of reasons. First, the analysis of transcripion start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. Secondly, it has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to much suboptimal levels of transcription.

Leaving in these transcribed sequences does allow determining the transcription rates, but potentially alters the stability of the reporter mRNA and influences translation initiation rates of an eventual open reading frame.

The role of this analysis, however, is the determination of the relative level of constitutive expression of a heterologous protein, as is the most frequent used application in biotechnology. Therefore the most important parameter is the ability of the tested sequences to drive high level expression of a heterologous reporter protein.

This would involve coupling the coding sequences of a reporter protein to the transcription activating part, promoter and 5' untranslated sequence of the gene which is tested for its properties. In this way a complex set of effects (combining transcription rates, mRNA stability (and thus degradation rates of the mRNA) and translational initiation rates) is reduced to one value that is a very useful value for determining usefulness of the tested gene elements in biotechnological applications.

There is no current word or phrase to describe this value. In the course of this application next to the term 'expression value' the terms 'expression level' and 'transcriptional activity' are used. We realize that this may cause some confusion. In all cases we do indicate with these and related terms the value just mentioned. A commonly used procedure to analyse expression patterns and levels is then through determination of the 'steady state' level of protein accumulation in a cell. Commonly used candidates for the reporter gene, known to those skilled in the art are β-glucuronidase (GUS), Chloramphenicol Acetyl Transferase (CAT) and proteins with fluorescent properties, such as Green Fluorescent Protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on e.g. immunochemical, enzymatic, fluorescent detection and quantification. Protein levels can be determined in plant tissue extracts or in intact tissue using in situ analysis of protein expression.

Generally, individual transformed lines with one chimeric promoter-reporter construct will vary in their levels of expression of the reporter gene. Also frequently observed is the phenomenon that such transformants do not express any detectable product (RNA or protein). The variability in expression is commonly ascribed to 'position effects' although the molecular mechanisms underlying this inactivity are usually not clear.

The term average expression is used here as the average level of expression found in all lines that do express detectable amounts of reporter gene, so leaving out of the analysis plants that do not express any detectable reporter mRNA or -protein.

Root expression level indicates the expression level found in protein extracts of complete plant roots. Likewise, 'leaf' and 'stem expression levels' are determined using whole extracts from leaves and stems. It is acknowledged however, that within each of the plant parts just described, cells with variable functions may exist, in which promoter activity may vary.

For the promoters described in this application the expression levels in large plant parts, containing cells with various functions, are measured. However, more detailed analyses may contribute to construction of a promoter that is even 'more constitutive' taking into account that more celltypes within a plant part are taken into account.

As a standard for judging expression levels the 35S promoter of the Cauliflower Mosaic Virus is a convenient and widespread used standard. The average expression level of this promoter may be classified as medium high.

The invention shows that it is possible to combine elements from one promoter which are responsible for a specific expression with elements from another promoter which are responsible for a complementary expression pattern to form a promoter which—as a result—shows expression in the tissues and developmental stages which form part of the expression pattern of both promoters. If the complementation results in activity in (nearly) all the cells of the plant, such complementation will yield a constitutive promoter. It seems to be necessary, however, that both promoters have a low expression value in the tissues and developmental stages which are specific for the other promoter. It has been established that, for being suitable, the transcriptional activity in the plant parts where expression is low should be preferably $\geq 1\%$ of the level of transcription which is reached in the plant parts where transcriptional activity is high.

This limits the availability of promoters and promoter elements from which to build a new constitutive promoter. A suitable promoter-pairs which fulfills the above mentioned criteria is:

the ferredoxin promoter in combination with the rolD promoter the S-adenosyl methionine promoter in combination with the plastocyanin promoter Other promoter-pairs which are complementary and which show at least some expression in the tissues and developmental stages which are specific for the other promoter can also be applied.

Delineation of Promoter and/or Enhancer Parts Needed.

Whereas transcription-regulating elements, especially in eukaryotes, may be present at large distances from the promoter/transcription initiation site, and located both downstream or upstream of the initiation site, many plant genes have most of their regulatory elements in the area directly upstream of the promoter. In order to identify the main transcription-activating elements of promoters it is common procedure to link parts of the non-transcribed areas that are found upstream (and downstream) of the promoter to a reporter gene, to analyse the ability of each of the truncated DNA elements to direct expression of that reporter. For delineation of more promoter-proximal sequences involved in transcription regulation, fragments of the enhancer sequences are most commonly coupled to a promoter, which may be derived from the gene of which transcription regulation is studied. Alternatively, a heterologous promoter can be used such as the sequences of the 35S promoter from −46 to +4, relative to the transcription start, which is functionally coupled to a reporter gene as described above.

In this way it is possible to delineate the transcription activating elements of most genes, a process that is well-known to those skilled in the art.

A large number of transcription regulatory elements of genes have been analysed in such a manner, and data relevant for this analysis are directly available to those skilled in the art through scientific publications.

Transcription activating elements that on average can direct expression to approximately the average level of the 35S promoter (at least 50% of this level) in at least some of the plant parts, and that are also capable of directing at least 0.5% (of the 35S level) transcription in other plant parts are then selected for further use.

The minimal promoter element is typically derived from one of the promoters of the promoter-pair, although not necessarily. It can be envisaged that such a minimal element is derived from a third promoter or is even made synthetically.

Based on the results of the analysis described above, transcription activating parts with complementary activities are selected. That is, for example, a promoter with expression throughout the plant, transcription activating DNA fragments that direct high level root expression and with lower leaf and stem expression levels, are combined with elements that direct expression mainly in the leaf and stem, but lower in the root. Other combinations of complementary transcription activating parts are obvious.

Preferentially, the level of expression in the parts where expression is lowest does not fall below 1% of the level obtained in the highest part. More preferred is the situation where the relation between lowest expression and highest expression between plant parts is larger than 5%.

This coupling can most easily be done by known genetic engineering techniques. The gene which has to be expressed by the new constutive promoter can be cloned behind the promoter. It is adviseable to build in a unique NcoI-cloning site at the linkage of the 5' untranslated sequence attached to the promoter to allow precise junction of the open reading frame (ORF) and the 3' end of the promoter in which the gene of interest can be inserted.

The Ferredoxin-RolD pair.

One of the preferred combinations of the present invention is a constitutive plant promoter comprising elements of both the ferredoxin promoter and the rolD-promoter. Preferably the ferredoxin promoter is obtained from *Arabidopsis* thaliana where it drives the ferredoxin A gene, a gene which is involved in the photosynthesis. The expression of this gene and the responsiveness of its promoter to light has been reported (Vorst, O. et al., Plant Mol. Biol. 14, 491–499, 1990; Vorst, O. et al., The Plant J. 3(6), 793–803, 1993; Dickey, L. F. et al.. The Plant Cell 6, 1171–1176, 1994). Since the ferredoxin gene is involved in photosynthesis the promoter is most active in green tissue. mRNA levels were shown to be high in chloroplast-containing organs such as stem, leaves and bracts, but also in young growing tissues, such as whole flowers and seedlings. Interestingly, there is a smaller, but significant expression in soilborne areas of the plant. The promoter sequence contains both a G-box and an I-box containing region. Also a potential Z-folding DNA sequence is found at position −182.

The rolD promoter is reported to have strong expression in the roots and is obtainable from *Agrobacterium rhizogenes*. Although the source organism is a bacterium, the promoter is very suitable for expression in plants because the bacterium is a phytopathogen which causes hairy-root disease in plants. For that purpose it transfers DNA to the plant amongst which the rolD gene is responsible for root elongation. To be expressable in plants this gene needed a strong promoter functional in plants, the rolD promoter. GUS-studies have shown that expression under control of the rolD-promoter yields mainly root-specificity (Leach, F. and Aoyagi, K., Plant Sci. 79, 69–76, 1991). Also, some expression in leaves was observed.

A combination of the ferredoxin and the rolD promoter can be obtained in two ways, depending on from which promoter the minimal promoter element and 5' untranslated sequences will be taken. In our examples we have used the minimal promoter element from the ferredoxin promoter, but deriving it from the rolD promoter is equally well possible.

The S-Adenosyl-Methonine Synthetase and Plastocyanin Pair.

Another favorable promoter can be obtained from a combination of the S-adenosyl-methionine synthetase (SAM) promoter and specific parts of the plastocyanin promoter. Preferably, both promoters are obtained from *Arabidopsis thaliana*.

The SAM promoter regulates the expression of S-adenosyl-methionine synthetase, which is an enzyme active in the synthesis of polyamines and ethylene. Promoter studies showed a strong expression in vascular tissues, in callus, sclerenchyma and some activity in root cortex (Peleman, J. et al., The Plant Cell 1, 81–93, 1989) which was reasoned to be due to the involvement of the enzyme in lignification.

The plastocyanin promoter, like the ferredoxin promoter, is also a promoter which is active in the photosynthetic pathway. mRNA levels are high in green, chloroplast-containing structures, such as leaves, cauline leaves, stem and whole seedling. Also in flowers the promoter is very active. Little expression is detectable in silique, seed and root (Vorst, O. et al., The Plant J. 4(6), 933–945, 1993).

By combining these specificities it is possible to create a chimeric promoter that drives good expression both in the photosynthetic areas of the leaf and stem, as well as in the area's not involved in photosynthesis, such as the cells forming and surrounding the vascular system in leaves and stems.

Other Pairs of Promoters.

The above given examples of promoter-pairs show in both cases the presence of a promoter which is active during photosynthesis. It is envisaged that other promoters which are regulating expression of a gene needed for photosynthetic activity may be suitable for a combination with either the rolD or other root-preferential promoters.

In the construction of a promoter that drives expression throughout the plant: if one of the components is a promoter which is more or less specific for green parts, this automatically means that the other promoter of the pair should be predominantly (but not exclusively) expressed in the roots and other non-photosynthesizing organs.

In the construction of a promoter that drives expression in all parts of leaves and stems, the combination may be made by using a promoter which is more or less specific for green parts and a promoter which drives expression primarily in the vascular system.

However, the invention is not limited to the combination of a root-preferential and a green part-preferential promoter, and a combination of green-part-preferential and vascular system-preferential promoters. All promoter combinations provided that the expression patterns of the individual promoters are complementary can be used.

It is also possible that the elements from which e.g. a new constitutive promoter is composed are derived from a set with more than two promoters. The above discussed complementarity should then also exist.

EXPERIMENTAL PART

EXAMPLE 1

Cloning of the Chimeric Fd-RolD Promoter

A 512 bp *Arabidopsis thaliana* ferredoxin promoter fragment (O. Vorst et al., 1990, PMB 14, 491–499.) ranging from position −512 to +4 (relative to the ATG startcodon of the ferredoxin Open Reading Frame) was isolated by digestion with HincII and NcoI. This fragment contains most of the transcriptional regulatory sequences of the ferredoxin promoter, the promoter sequences and leader of the ferredoxin transcript. An XbaI site was introduced, for cloning reasons, at positions −5 to −10 relative to the ATG (O. Vorst et al., 1990, PMB 14, 491–499.). This changes the original sequence of the clone at this point from ACAAAA to TCTAGA (SEQ ID NO: 1).

Part of the *Agrobacterium rhizogenes* rolD upstream sequences (SEQ ID NO: 2) (Leach et al., 1991 Plant Sci. 79, 69–76) were fused to the ferredoxin promoter sequences described above. A HindIII-RsaI fragment, comprising nucleotides −385 to −86 relative to the initiation codon was cloned next to the ferredoxin fragment, joining the RsaI sites of the latter with the HincII site of the former. This chimaeric element, containing the promoter and some of the activating sequences of the ferredoxin gene, and upstream activating sequences of the rolD gene was used in subsequent studies as to its transcription-stimulating properties (SEQ ID NO: 3).

EXAMPLE 2

GUS-Fusions

The Fd-rolD chimaeric promoter/activator was coupled to the GUS gene, engineered to contain an intron gene (Jefferson et al., (1987) EMBO J. 6: 3901–3907). The NcoI restriction site on the ATG start codon was used to join the promoter to the Open Reading Frame (ORF) of the GUS gene, coupled to a 265 bp fragment containing the Proteinase Inhibitor II 3' untranslated and transcriptional termination sequences (Thornburg et al., 1987, Proc. Natl. Acad. Sci. USA 84, 744–748; An et al., Plant Cell 1, 115–122.

The whole expression cassette, containing the promoter, GUS gene and 3' PI-II sequences was cloned out using BamHI and EcoRI and introduced into the binary vector pMOG800 (deposited at the Centraal Bureau voor Schimmelcultures, Baarn, The Netherlands, under CBS 414.93, on Aug. 12, 1993) digested with the same enzymes. The subsequently made construct (pMOG1059) was used in transformation experiments with various plants. As a control a 35S CaMV promoter-GUS construct was used. This is construct pMOG410. A schematic representation of both constructs is found in FIG. 1.

EXAMPLE 3

Expression Levels and Patterns of Promoter Activity During Early Stages of Plant Transformation First, *Arabidopsis thaliana* transformants were made with both constructs and GUS expression was followed in time during the transformation procedure.

GUS expression levels were determined visually, on a scale of 0 to 5, where 0 is no detectable expression and 5 is the highest level of GUS we have observed in leaves of a transgenic plant, of a rare tobacco 35S-GUS-transgenic (line 96306). Samples from leaves of this plant were included in all experiments for internal reference.

In table 1 the relative GUS expression in *Arabidopsis thaliana* explants is indicated, at several times after *Agrobacterium tumefaciens* cocultivation (DAC; days after cocultivation)

TABLE 1 relative GUS activity of *Arabidopsis* root explants.

| Time of assay | Construct: | |
|---|---|---|
| | pMOG1059 | pMOG410 |
| DAC 0 | 2 | 3 |
| DAC 2 | 3 | 3 |
| DAC 5 | 3 | 3 |
| DAC 7 | 4 | 3 |
| DAC 9 | 4 | 3 |
| DAC 12 | 4 | 3 |

As can be seen from this comparison, GUS expression driven by the chimaeric promoter starts slightly later after cocultivation but from day 7 on, exceeds the level of expression obtained with the reference 35S promoter.

Very similar data were obtained when: *Brassica napus* explants were scored for GUS expression. At day 5 after co-cultivation the 35S promoter is slightly higher, but the situation is reversed on day 20 after co-cultivation. Also for tomato similar data were obtained. Here even at the earliest stage of analysis expression of pMOG1059-transgenics exceeded that of pMOG410 transgenics.

EXAMPLE 4

Expression Levels and Patterns in In Vitro Grown Plants

When plants are grown up further, differences between these promoters become ever clearer. Leaf samples of fully regenerated plants were analysed for GUS expression. Averages were obtained from 11–48 plants, dependent on the construct.

For *Arabidopsis thaliana* that was grown in vitro only, no large difference was observed between GUS expression in pMOG1059 and pMOG410-transgenics.

TABLE 2

Average relative GUS activity of leaf samples of all tested crops.

| | Construct: | |
|---|---|---|
| Crop: | pMOG1059 | pMOG410 |
| Potato | 4.0 | 2.1 |
| *Brassica napus* | 3.7 | 2.8 |
| *Arabidopsis* | 4.0 | 4.1 |
| Tomato | 2.2 | 2.1 |

Figure 2:
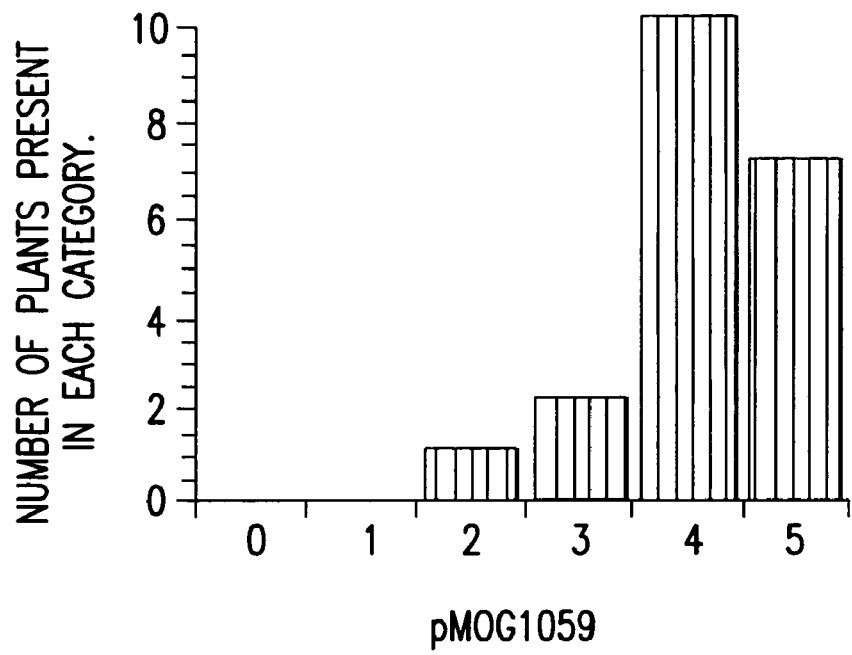
FIG. 2: Distribution of GUS expression of potato lines transformed with the constructs pMOG1059 en pMOG410. GUS staining was judged visually and classes of expression, relative to the highest GUS expression measured in our lab (set at 4). A value of zero indicates no visible expression.
Figure 2:
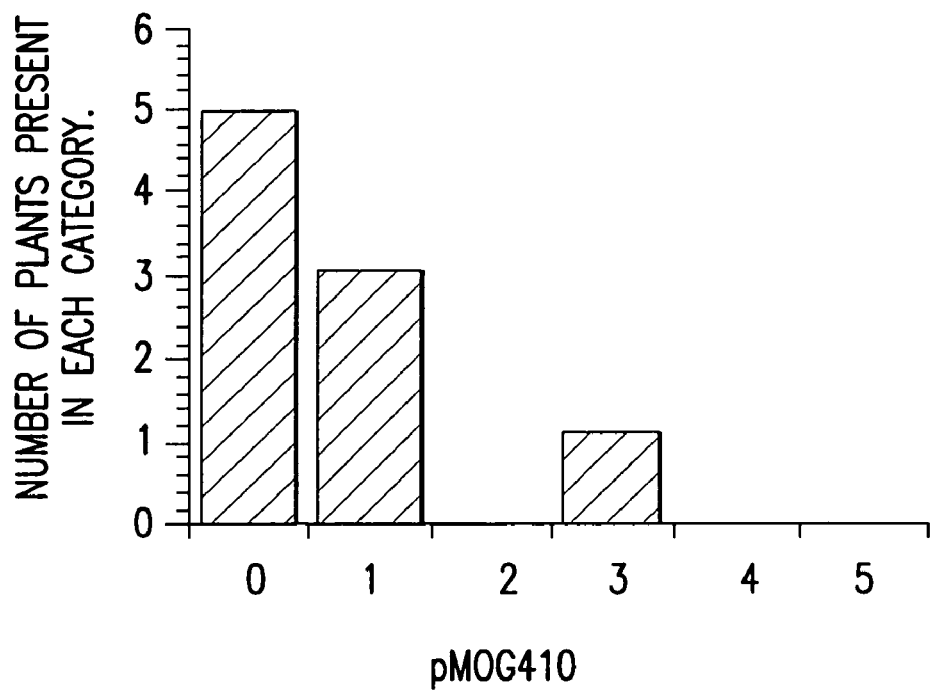

What is also clear from the data presented in FIG. 2 that a significant number of 35S-GUS transgenic lines (app. 50% was found repeatedly in our experiments) do not express GUS to a level that it is visible. So not only maximum and average expression are higher in the Fd-rolD-GUS transgenics, also the frequency with which transgenic plants do express GUS is strongly enhanced. In about 50 transgenic potato plants carrying the Fd-rolD-GUS construct, we have found no weak expressor, suggesting a reliable high expression in at least 98% of the lines made.

EXAMPLE 5

Comparison of Promoter Performance in Various Crops

Constructs pMOG410 (35S-GUS) and pMOG1059 (Fd-rolD-GUS) were also introduced into oilseed rape and tomato for a further comparison of promoter performance. Also the data for potato are included here.

Figure 3A:
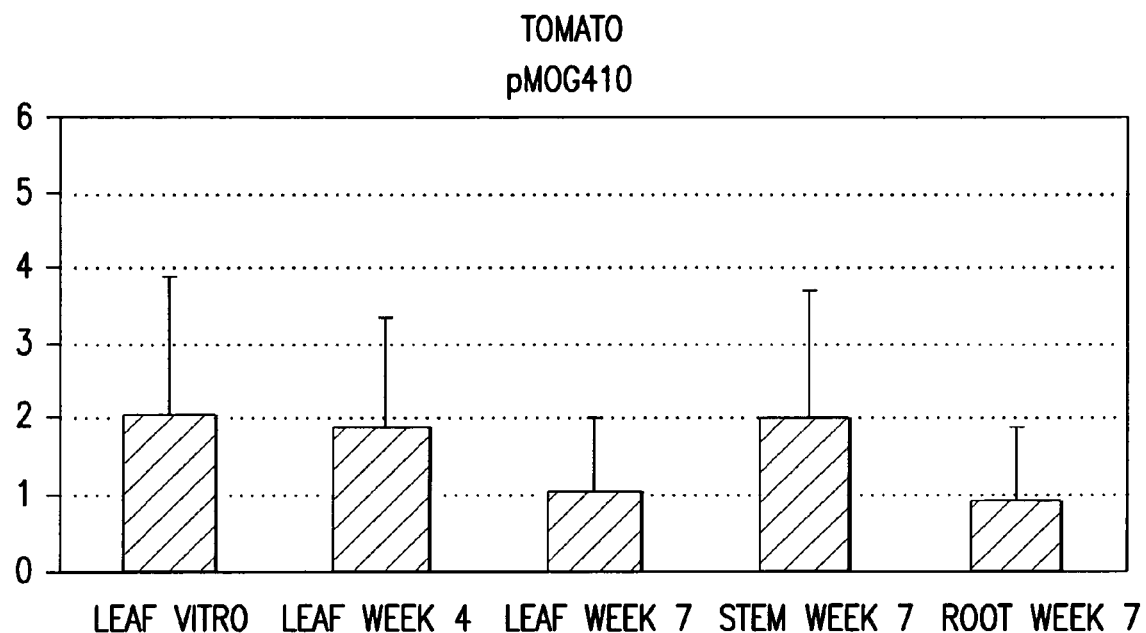
FIG. 3: Graphic representation of the average expression of GUS enzyme in primary transformants of (A) tomato, (B) oilseed rape and (C) potato. GUS expression was determined visually and compared to a high level expressing 35S GUS transgenic tobacco plant ranking a score of 4. Standard deviation of the measured values are indicated on each of the bars.
Figure 3A:
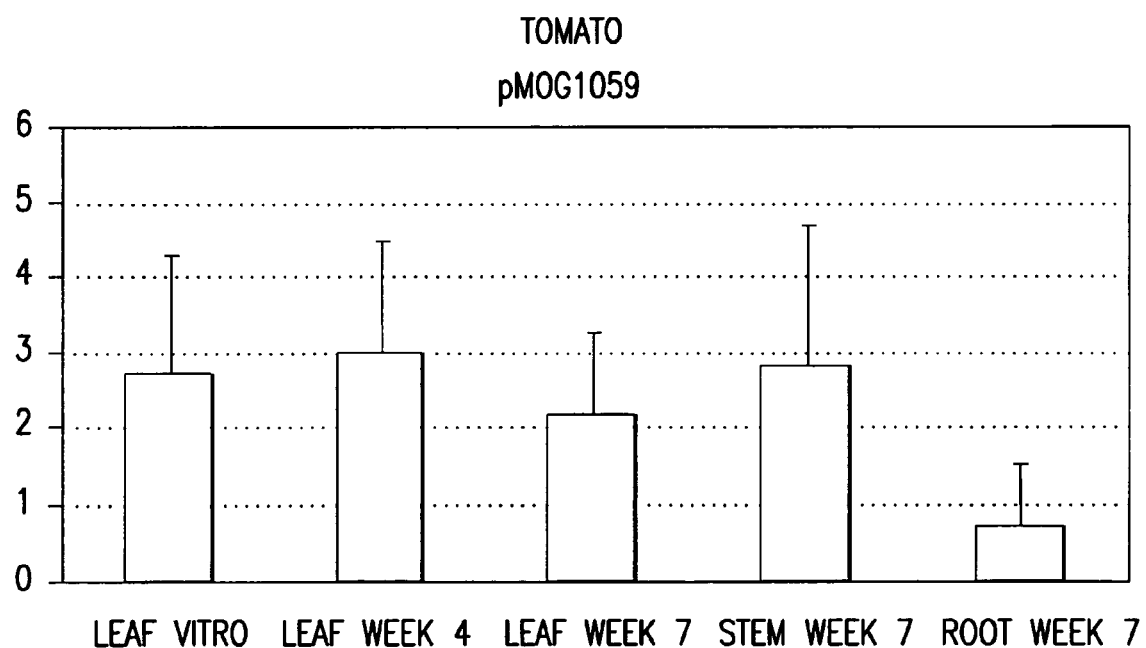

As shown in FIG. 3A, in tomato the overall level of expression of the Fd-rolD promoter is higher both at the latest stage of in vitro growth as well as in leaves of 4 and 7 week old plants. Also in stems of 7 weeks this holds true, however, for roots, an average weaker expression is observed with the Fd-rolD promoter than for the 35S promoter.

Figure 3B:
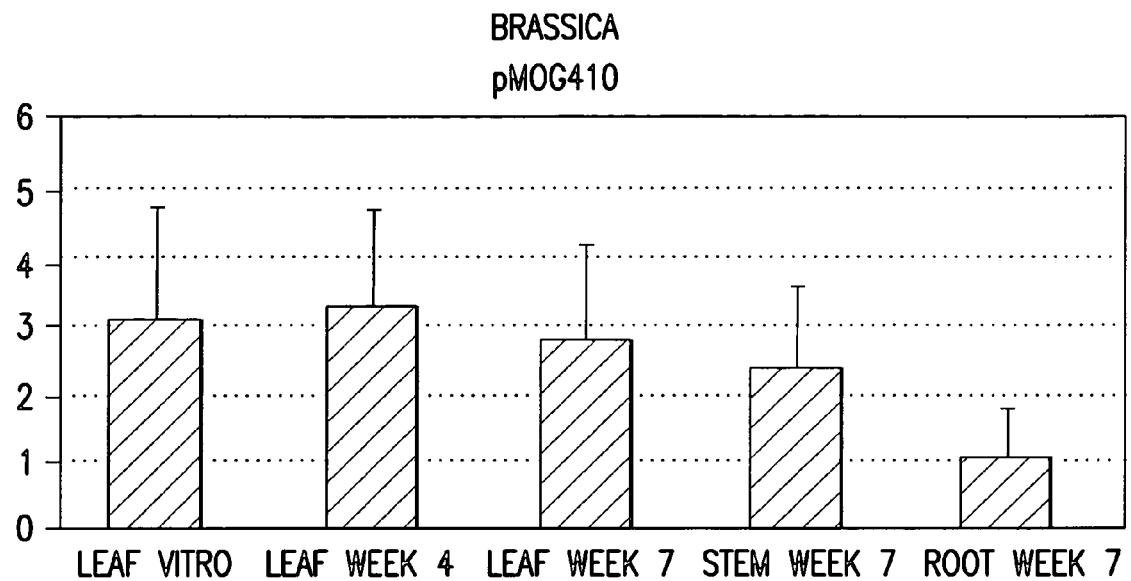
Figure 3B:
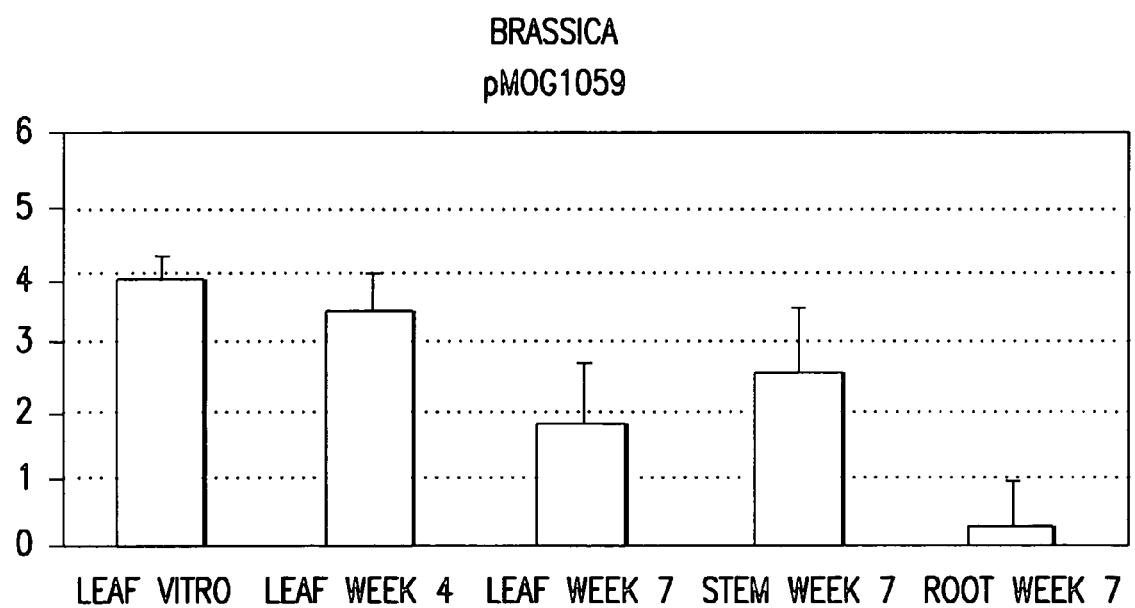
Figure 3C:
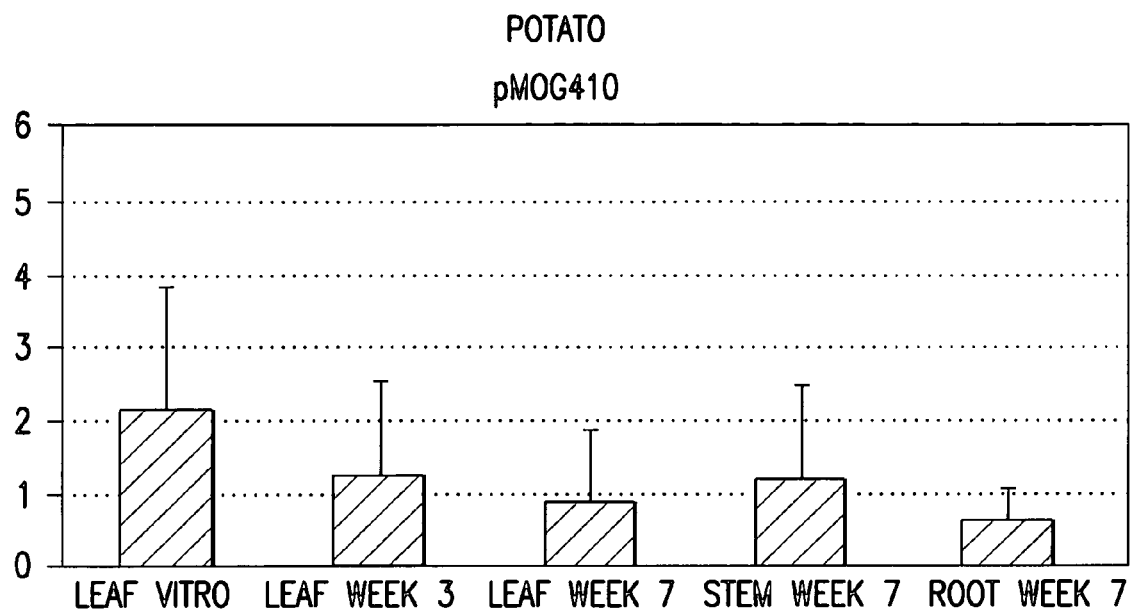
Figure 3C:
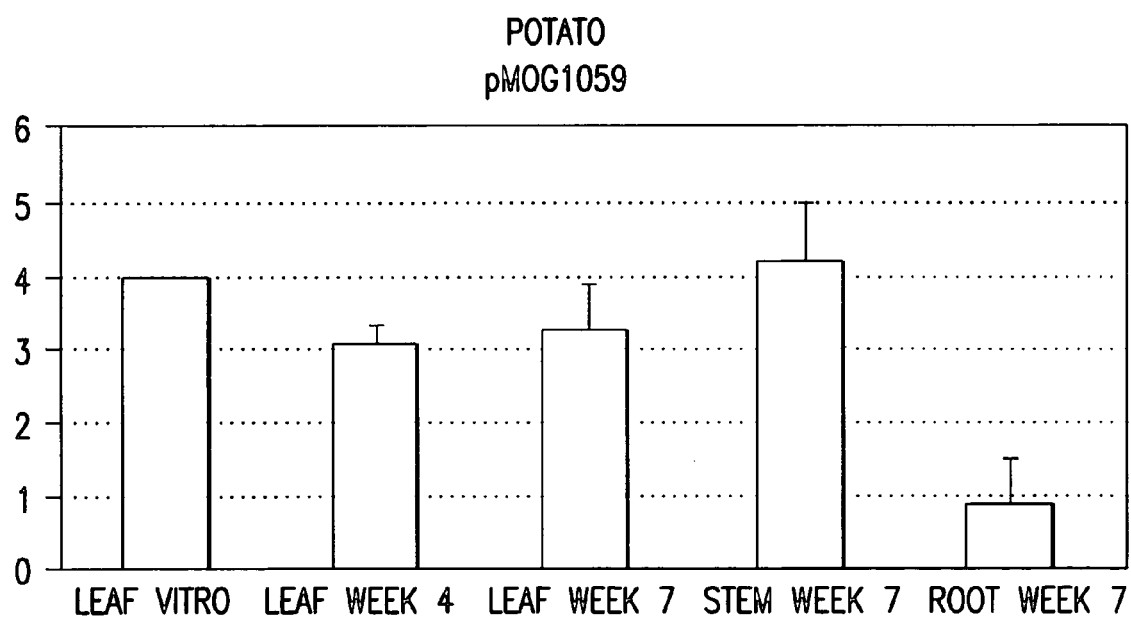

Also in oilseed rape and potato, similar results are obtained, with the notable exception that in potato roots the level of expression by the Fd-rolD promoter exceeds that of the 35S promoter. As shown in FIGS. 3B and 3C both the average expression of the Fd-rolD promoter is higher and also the variation in expression is significantly lower. In conclusion we can say we have created a promoter that withstands the comparison with the 35S promoter easily in three major crops.

EXAMPLE 6

Expression of nptII Transgene

In order to also check usability of the Fd-rolD promoter for other purposes, the promoter was linked to the nptII gene, of which expression of the corresponding gene product confers resistance in plants to the antibiotic kanamycin. This element was placed between the left and right borders of the T-DNA allowing *Agrobacterium tumefaciens*-mediated transfer to plants. As a control, similar constructs in which the expression of the nptII gene was under control of the nos promoter were used.

The resistance to kanamycin in transgenic potato plants is manifested by the development of transgenic calli and shoots during a standard transformation procedure, in which kanamycin is used in the culture medium.

On average, for the constructs with the nos-nptII selction cassette, the transformation frequency for potato is 45%, for constructs with the Fd-rolD-nptII selection cassette the frequency is on average 61%. While we do not know at this moment how relevant the increase in transformation frequency is for this construct, it indicates that the Fd-rolD promoter is at least as suitable for driving a heterologous gene such as nptII, as commonly used constitutive promoters such as nos.

EXAMPLE 7

Comparing Visual Scoring to Quantitative Values

From the analysis of GUS expression based on 1) histochemical analysis and scoring to an internal control and 2) to a quantitative analysis of GUS enzymatic activity, we have learned that both give a reproducible quantitative figure. A thorough analysis of both scores for tomato and oilseed rape leaves and roots, leads to the conclusion that scale 3, which compares best to that of 35S, equals about 2000 pmol MU/minute.mg made in the quantitative analysis. In scale 1 and 2, averages are 1000 and 1500, respectively, which set the value of 50% of 35S. About 1% expression of that level equals 100 pmol MU/minute.mg, which is frequently under the detection level for histochemical detection, although sometimes detectable as very light blue staining due to GUS expression. Therefore one can use histochemical staining as a marker for promoter efficacy, by measuring the level of blue staining, and use these data to select promoter elements of use.

EXAMPLE 8

Construction of the SAM1 Promoter and Fusion to GUS

For the construction of the SAM1 promoter genomic DNA (SEQ ID NO: 4) was isolated from *Arabidopsis thaliana* Landsberg erecta leaves using a CTAB extraction procedure. Primers were designed based on the published sequence of the SAM1 gene from *Arabidopsis thaliana* K85 (Peleman et al., (1989) Gene 84, 359–369). In a PCR (30 cycles of 45 seconds 95° C., 45 seconds 50° C. and 1' 72° C.; same program was used in all other PCR's described in this part) the promoter element was amplified using primers FR-Psam-143 5' AGA TTT GTA TTG CAG CGA TTT CAT TTT AG 3' (SEQ ID NO: 5) and FR-Psam-216 5' ATC TGG TCA CAG AGC TTG TC 3' (SEQ ID NO: 6) yielding a fragment of about 550 bp. The DNA fragment was isolated from an agarose gel and cloned into the pGEM-T vector (Promega Corp., Madison, Wis., USA). This clone was used as a template to introduce a Nco I site at the translation start by PCR using primers FR-Psam-144 5' GTC TCC ATG GTG CTA CAA AGA ATA G 3' (SEQ ID NO: 7) and FR-Psam-143. The resulting 500 bp fragment was cloned in the pGEM-T vector. The EcoR I and Hind III sites located in the promoter region were removed by PCR in two steps using this clone as a template. In this PCR a BamH I site was introduced upstream of the SAM1 promoter and a Hind III site was introduced at the 3' site of the promoter. In the first PCR step three promoter fragments were generated. The first fragment (1) will contain the 5' BamH I site and the mutated EcoR I site using primers FR-Psam-248 5'CGG GAT CCT GCA GCG ATT TCA TTT TAG 3' (SEQ ID NO: 8) and FR-Psam-249 5' ACA TGA ACG AAT GCA AAA TCT C 3' (SEQ ID NO: 9). The middle fragment (2) is obtained with primers FR-Psam-250 5' AGA TTT TGC ATT CGT TCA TGT G 3' (SEQ ID NO: 10) and FR-Psam-251 5' TGT AAG CAT TTC TTA GAT TCT C 3' (SEQ ID NO: 11). This fragment has a partial overlap with fragment 1 and 3 and has mutated EcoR I and Hind III sites. The third PCR fragment (3) will contain the mutated internal Hind III site and introduces a Hind III site at the 3' end of the promoter encompassing the Nco I site at the translation start and is generated using primers FR-Psam-252 5' AAG AAA TGC TTA CAG GAT ATG G 3' (SEQ ID NO: 12) and FR-Psam-253 5' GAC AAG CTT GAT CCC ATG GTG CTA CAA AGA ATA G 3' (SEQ ID NO: 13). In a second PCR the 3 fragments 1,2 and 3 were mixed together in one tube and amplified with primers FR-Psam-248 and FR-Psam-253. Due to the overlap between fragments 1 and 2, and 2 and 3, this PCR yields the complete mutated promoter. After digestion with BamH I and Hind III the resulting SAM1 promoter was cloned in a pBSK+ vector. The SAM1 promoter was then cloned into a vector containing a GUSintron-TPI-II reporter cassette by exchanging the upstream region using the BamH I and Nco I restriction sites. This was done by digestion of the SAM1 clone with BamH I and Nco I and isolation of the promoter fragment from a agarose gel. The GUS vector was digested with the same enzymes and the vector was then isolated from a agarose gel thus discarding the original upstream sequences promoter.

The SAM1 promoter-GUSintron-TPI-II reporter cassette was then cut out of the vector by BamH I and EcoR I digestion after which the reporter cassette was isolated from a agarose gel and cloned into the binary vector pMOG800 digested with BamH I and EcoR I. The resulting binary vector pMOG1402 was introduced in *Agrobacterium tumefaciens* strain EHA105 for transformation to potato.

EXAMPLE 9

Construction of the Pc-SAM1 Chimaeric Promoter and Fusion to the GUS Gene

The plastocyanin enhancer (Pc) from *Arabidopsis thaliana* Col-0 was obtained by PCR. Therefore primer FR-Pc-146 (5' agt ggt acc atc ata ata ctc atc ctc ctt ca3') (SEQ ID NO: 14) and primer FR-Pc-247 (5' cga agc ttt aca aat cta att tca tca cta aat cgg a3') (SEQ ID NO: 15) were developed introducing a Kpn I restriction site upstream of the enhancer and a Hind III restriction site downstream of the plastocyanin enhancer. The PCR was performed using Cloned pfu DNA polymerase (Stratagene) for 30 cycles 1' 95° C., 1' 50° C., 4' 72° C. and 1 cycle 1' 95° C., 1' 50° C., 10' 72° C. The resulting PCR fragment was ligated into a high copy cloning vector using Kpn I and Hind III resulting in construct pPM15.1.

This clone was used as a template for a PCR (30 cycles of 1' 95° C., 1' 50° C. and 21 72° C.) using primers FR-Pc-145 5' GCT GCA ATA CAA ATC TAA TTT CAT CAC TAA ATC GG 3' (SEQ ID NO: 16) and FR-Pc-146 5' AGT GGT ACC ATC ATA ATA CTC ATC CTC CTT C$_3$' (SEQ ID NO: 14). The PCR generates a fragment of about 850 bp encompassing the Pc enhancer (SEQ ID NO: 17) containing a upstream Kpn I site and overlap with the 5' side of the SAM1 promoter (see Example 8). The PCR fragment was then mixed with a PCR fragment of the SAM1 promoter generated with primers FR-Psam-143 and FR-Psam-144 using the pBKS+ clone containg the adjusted SAM1 promoter described in example 8. In a PCR on this mixture the PcSAM chimeric promoter was generated using primers FR-Psam-144 and FR-Pc-146. The resulting promoter fragment of about 1.3 kb (SEQ ID NO: 18) was isolated from a agarose gel after digestion with Kpn I and Nco I and then cloned into a high copy cloning vector (pUC28) digested with the same enzymes. The promoter fragment was then cut out of this vector by digestion with BamHI and NcoI and cloned in front of the GUSintron gene as described above in Example 8. The complete Pc-SAM-GUS-TPI-II reporter cassette was then cloned into pMOG800 as described for the SAM1-GUS-TPI-II reporter cassette in Example 8. The resulting binary vector pMOG1400 was introduced in *Agrobacterium tumefaciens* strain EHA105 for transformation to potato.

EXAMPLE 10

Construction of the Pc Enhancer-35S Promoter and Fusion to the GUS Gene

The plastocyanin enhancer (Pc) from *Arabidopsis thaliana* Col-0 was obtained by PCR (see above).

This clone was used as a template for a PCR (30 cycles of 1' 95° C., 1' 50° C. and 2' 72° C.; all other PCR reactions described in this part were carried out with the same program) using primers FR-Pc-291 5' GTC TTG TAC AAA TCT AAT TTC ATC ACT AAA TCG G 3' (SEQ ID NO: 19) and FR-Pc-146 5' AGT GGT ACC ATC ATA ATA CTC ATC CTC CTT C 3' (SEQ ID NO: 14). The PCR generates a fragment of about 850 bp encompassing the Pc enhancer containing a upstream KpnI site and overlap with the 5' side of the minimal 35S promoter. The minimal 35S promoter was obtained in a PCR using pMOG971 as a template (containing the 35S promoter and omega 5' UTR) and primers FR-35S-292 5' TTA GAT TTG TAC AAG ACC CTT CCT CTA TAT AAG G 3' (SEQ ID NO: 20) and ls19 (SEQ ID NO: 21). The resulting fragment has overlap with the Pc enhancer and contains a internal NcoI site at the translation start. The two PCR fragments were then mixed and a PCR reaction was carried out using primers FR-Pc-146 and ls19. The resulting fragment was then digested with KpnI and NcoI, isolated from a agarose gel and cloned in pUC28 digested with the same enzymes. The resulting clone was, subsequently, digested with BamHI and NcoI, and the promoter fragment (SEQ ID NO: 22) was isolated from a agarose gel and cloned upstream of the GUS gene as described in Example 7. The complete reporter cassette was then introduced in the binary vector pMOG800 as described in Example 7. The resulting binary vector pMOG1401 was introduced in *Agrobacterium tumefaciens* strain EHA105 for transformation to potato.

EXAMPLE 11

Expression Levels and Patterns in In Vitro Grown Plants

Figure 4:
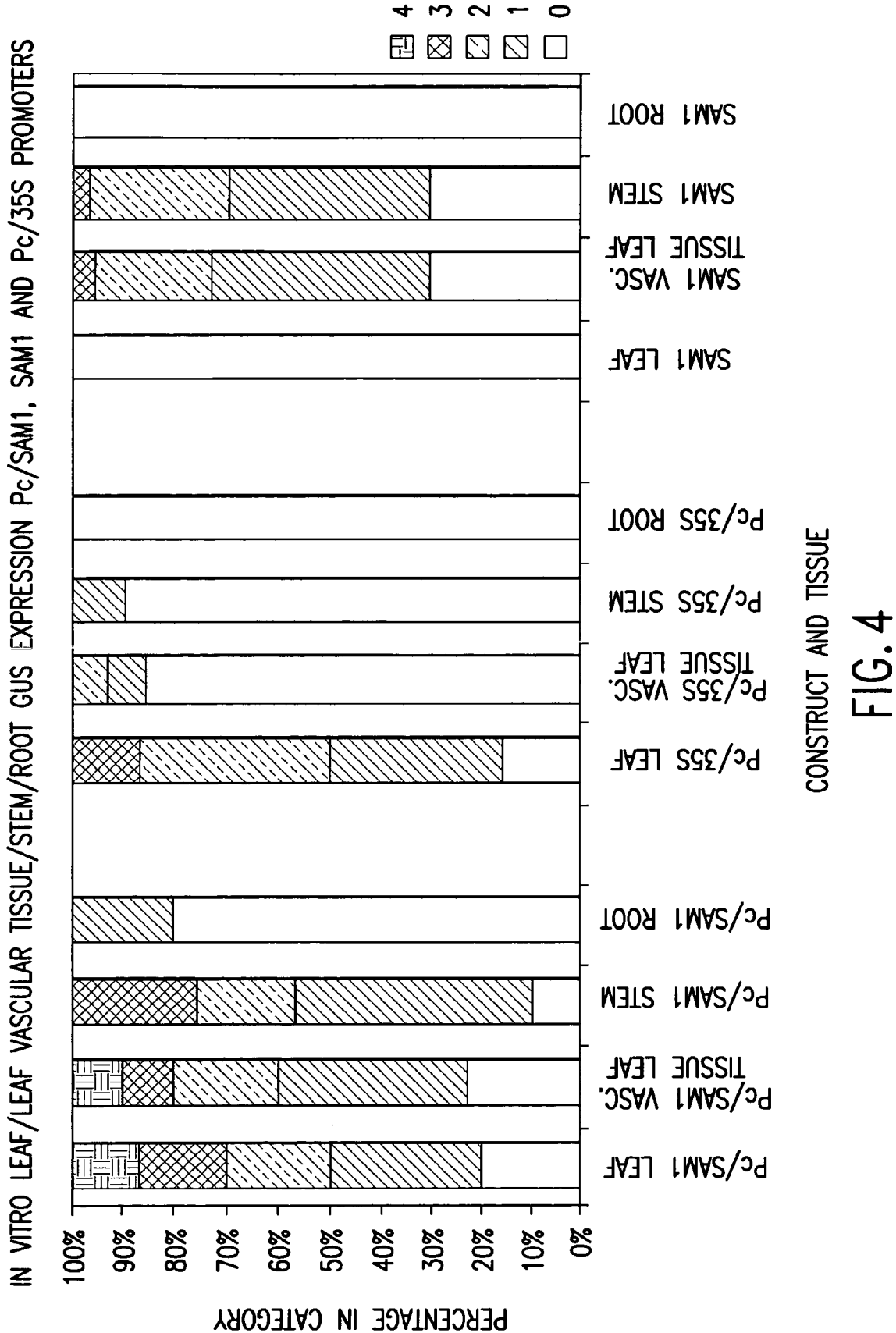
FIG. 4: Graphic representation of the distribution of potato plants with various levels of GUS expression containing SAM-1-, Pc-35S- and PcSAM1-GUS constructs. Scored are expression in leaf mesophyll, leaf vascular system, stem and root.

Transformed plants were grown up, and leaf samples of fully regenerated plants were analyzed for GUS expression. In FIG. 4 the analysis of expression in leaf mesophyll, leaf vascular system, stems and roots is indicated. A very low level of GUS staining was observed in the mesophyll part of leaves of SAM1-transgenic plants although the scoring indicates a GUS expression level of 0.

What is claimed:

1. A plant promoter comprising (1) a minimal promoter comprising a TATA box and initiation site, (2) transcription-activating elements from a first promoter and (3) transcription-activating elements from a second promoter wherein said first promoter is a ferredoxin promoter and said second promoter is a RolD promoter.

2. The plant promoter according to claim 1 wherein the minimal promoter ferredoxin minimal promoter.

3. The plant promoter according to claim 1 wherein the ferredoxin promoter is an *Arabidopsis thaliana* ferredoxin promoter.

4. The plant promoter according to claim 3 comprising SEQ ID NO:1 and SEQ ID NO:2.

5. The plant promoter according to claim 3 comprising SEQ ID NO:3.

6. A chimeric gene construct comprising the plant promoter of claim 1.

7. The plant promoter according to claim 1 wherein the minimal promoter is a RolD minimal promoter.

8. The plant promoter according to claim 1 wherein the RolD promoter is an *Agrobacterium rhizogenes* RolD promoter.

* * * * *

SEQUENCE LISTING

<160> NUMBER OF SEQ ID NOS: 22

<210> SEQ ID NO 1
<211> LENGTH: 520
<212> TYPE: DNA
<213> ORGANISM: Arabidopsis thaliana

<400> SEQUENCE: 1

```
gactgaagtg tgaaggtgga gattatgtat tcacttgttg atttggtata cattctatgt      60
aaggttcaat tatttacgtt atataattat aatggagtaa tttacagtaa ttgggttaaa     120
atggtttgat tcggtcaggt tgatacggtt tggaagttaa acccggccta gatatgatgt     180
tacaaccagt ccacatcttt tatgatttta gtggaacaaa cgaagagtta tttagacgat     240
acaaacaagg tccgaataag tgtgagctgt cccaagtaag accacgtaat actcacctca     300
acaagatagt gttcttaaag tgtgtcaaac acaatcacac acacaaaat cataaaacac      360 aaagacgata atccatcgat ccacagaata gacgccacgt ggtagatagg attctcacta     420
aaaagttctc acctttaat ctttctccac gccatttcca caagccataa tcctcaaaaa      480 tctcaactt atctcccaaa acacaaatct agaaaccatg                            520
```

<210> SEQ ID NO 2
<211> LENGTH: 300
<212> TYPE: DNA

-continued

<213> ORGANISM: Agrobacterium rhizogenes

<400> SEQUENCE: 2

| cccactacaa tgaatttgtt cgtgaactat tagttgcggg ccttggcatc cgactacctc | 60 |
| tgcggcaata ttatattccc tgggcccacc gtgaacccaa tttcgcctat ttattcatta | 120 |
| cccccattaa cattgaagta gtcatgatgg gcctgcagca cgttggtgag gctggcacaa | 180 |
| ctcatccata tactttctga ccggatcggc acattattgt agaaaacgcg gacccacagc | 240 |
| gcactttcca aagcggtgcc gcgtcagaat gcgctggcag aaaaaaatta atccaaaagt | 300 |

<210> SEQ ID NO 3
<211> LENGTH: 840
<212> TYPE: DNA
<213> ORGANISM: Artificial
<220> FEATURE:
<223> OTHER INFORMATION: Chimeric promoter

<400> SEQUENCE: 3

| ggatccgagc ttgcatgccc ccactacaat gaatttgttc gtgaactatt agttgcgggc | 60 |
| cttggcatcc gactacctct gcggcaatat tatattccct gggcccaccg tgaacccaat | 120 |
| ttcgcctatt tattcattac ccccattaac attgaagtag tcatgatggg cctgcagcac | 180 |
| gttggtgagg ctggcacaac tcatccatat actttctgac cggatcggca cattattgta | 240 |
| gaaaacgcgg acccacagcg cactttccaa agcggtgccg cgtcagaatg cgctggcaga | 300 |
| aaaaaattaa tccaaaagtg actgaagtgt gaaggtggag attatgtatt cacttgttga | 360 |
| tttggtatac attctatgta aggttcaatt atttacgtta tataattata atggagtaat | 420 |
| ttacagtaat tgggttaaaa tggtttgatt cggtcaggtt gatacggttt ggaagttaaa | 480 |
| cccggcctag atatgatgtt acaaccagtc cacatctttt atgattttag tggaacaaac | 540 |
| gaagagttat ttagacgata caaacaaggt ccgaataagt gtgagctgtc caagtaaga | 600 |
| ccacgtaata ctcacctcaa caagatagtg ttcttaaagt gtgtcaaaca caatcacaca | 660 |
| cacacaaatc ataaaacaca aagacgataa tccatcgatc cacagaatag acgccacgtg | 720 |
| gtagatagga ttctcactaa aaagttctca cctttttaatc tttctccacg ccatttccac | 780 |
| aagccataat cctcaaaaat ctcaacttta tctcccaaaa cacaaatcta gaaaccatgg | 840 |

<210> SEQ ID NO 4
<211> LENGTH: 477
<212> TYPE: DNA
<213> ORGANISM: Arabidopsis thaliana

<400> SEQUENCE: 4

| ggatcctgca gcgatttcat tttagattct caaaaatatt ctcagatgtg tgggatttga | 60 |
| gtagagttta tgttgcgttg gcatgatttg aatagtatgc aagatttttg agattttgca | 120 |
| ttcgttcatg tgtgtatgtg tgattgtagc ttgatatgat ttaacctgtt agttaaatgt | 180 |
| gcatagacaa taagtaacat acgaagcgag tcactaagca taagagtcaa cttgttttgc | 240 |
| tgaaaagata tcacttatga ttttcgaatc attttagctt ttttgtcact tgagcttaat | 300 |
| gattcttctg aaattcgatt ctttgtttgg tttatgtcac attctttaga attgagaatc | 360 |
| taagaaatgc ttacaggata tggtgaaact attcttttaa gatagcatga tgcttctttt | 420 |
| atgattctac agtggctaag tcattttttt tttgttctat tctttgtagc accatgg | 477 |

<210> SEQ ID NO 5
<211> LENGTH: 29

```
<212> TYPE: DNA
<213> ORGANISM: Artificial
<220> FEATURE:
<223> OTHER INFORMATION: Primer

<400> SEQUENCE: 5
agatttgtat tgcagcgatt tcattttag                                29

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
atctggtcac agagcttgtc                                          20

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
gtctccatgg tgctacaaag aatag                                    25

<210> SEQ ID NO 8
<211> LENGTH: 27
<212> TYPE: DNA
<213> ORGANISM: Artificial
<220> FEATURE:
<223> OTHER INFORMATION: Primer

<400> SEQUENCE: 8
cgggatcctg cagcgatttc attttag                                  27

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
acatgaacga atgcaaaatc tc                                       22

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
agattttgca ttcgttcatg tg                                       22

<210> SEQ ID NO 11
<211> LENGTH: 22
<212> TYPE: DNA
<213> ORGANISM: Artificial
<220> FEATURE:
<223> OTHER INFORMATION: Primer

<400> SEQUENCE: 11
```

-continued tgtaagcatt tcttagattc tc                                                22

<210> SEQ ID NO 12
<211> LENGTH: 22
<212> TYPE: DNA
<213> ORGANISM: Artificial
<220> FEATURE:
<223> OTHER INFORMATION: Primer

<400> SEQUENCE: 12
aagaaatgct tacaggatat gg                                                22

<210> SEQ ID NO 13
<211> LENGTH: 34
<212> TYPE: DNA
<213> ORGANISM: Artificial
<220> FEATURE:
<223> OTHER INFORMATION: Primer

<400> SEQUENCE: 13
gacaagcttg atcccatggt gctacaaaga atag                                   34

<210> SEQ ID NO 14
<211> LENGTH: 31
<212> TYPE: DNA
<213> ORGANISM: Artificial
<220> FEATURE:
<223> OTHER INFORMATION: Primer

<400> SEQUENCE: 14
agtggtacca tcataatact catcctcctt c                                      31

<210> SEQ ID NO 15
<211> LENGTH: 37
<212> TYPE: DNA
<213> ORGANISM: Artificial
<220> FEATURE:
<223> OTHER INFORMATION: Primer

<400> SEQUENCE: 15
cgaagcttta caaatctaat ttcatcacta aatcgga                                37

<210> SEQ ID NO 16
<211> LENGTH: 35
<212> TYPE: DNA
<213> ORGANISM: Artificial
<220> FEATURE:
<223> OTHER INFORMATION: Primer

<400> SEQUENCE: 16
gctgcaatac aaatctaatt tcatcactaa atcgg                                  35

<210> SEQ ID NO 17
<211> LENGTH: 876
<212> TYPE: DNA
<213> ORGANISM: Arabidopsis thaliana

<400> SEQUENCE: 17
atcataatac tcatcctcct tctcaaggtt cgtacgtatt atcaatatct agtatatact        60
tgtctttgtt ctatgcttta tatcatcatt ttatgacaaa aaatgattaa ggtcttagtt       120
aatgattatg tatatgtgaa acttatattt aggggcacaa tttaatttcg tatgataatt       180
gtctagttag cttttgtgtac ttatcataaa aaccttagtg tttatcgcaa tacttttcaa      240
atatagtgta gaatcataat ggtcccactg tcattatgtt tgatgcaaat ctatttggat      300

-continued

```
tttgttggat aataaaccga tgacgtggac cagaccagta gctataagat ttggttcaca      360
tagaaatttt ttataagata atgtatctag gtttgcttat gattatacat gtgatattta      420
atacatggca caggttcgtc gagttttcaca gccataggta caatagaagg caaattcgat     480
tgtggttatc tggtaaaagt taagttgggc tcagagattc ttaacggcgt tctttatcat     540
tcggcccagc ccggcccatc atcatctcca accgctgttc taaacaatgc cgttgtacct    600
tatgttgaaa ctgggaggag acggcgtcgt ttaggtaaaa gacgaagaag cagacgcaga    660
gaagatccga attcccgaa accgaaccgg agcggttaca atttcttctt tgctgagaaa      720
cattgcaagc tcaaatcact ttatcccaac aaggagagag agtttacgaa acttatcgga     780
gaatcgtgga gcaatctctc taccgaagaa cgaatggtaa caaattatct tttaaaccgt     840
taccgattta gtgatgaaat tagatttgta gtaaat                               876
```

<210> SEQ ID NO 18
<211> LENGTH: 1357
<212> TYPE: DNA
<213> ORGANISM: Arabidopsis thaliana

<400> SEQUENCE: 18

```
ggatccccgg gtaccatcat aatactcatc ctccttctca aggttcgtac gtattatcaa      60
tatctagtat atacttgtct tgttctatg ctttatatca tcattttatg acaaaaaatg     120
attaaggtct tagttaatga ttatgtatat gtgaaactta tatttagggg cacagtttaa     180
tttcgtatga taattgtcta gttagcttta tgtacttatc ataaaaacct tagtgtttat     240
cgcaatactt tcaaatata gtgtagaatc ataatggtcc cactgtcatt atgtttgatg     300
caaatctatt tggattttgt tggataataa accgatgacg tggaccagac cagtagctat    360
aagatttggt tcacatagaa attttttata agataatgta tctaggttg cttatgatta     420 tacatgtgat atttaataca tggcacaggt tcgtcgagtt tcacagccat aggtacaata    480
gaaggcaaat tcgattgtgg ttatctggta aaagttaagt tgggctcaga gattcttaac    540
ggcgttcttt atcattcggc ccagcccggc ccatcatcat ctccaaccgc tgttctaaac    600
aatgccgttg taccttatgt tgaaactggg aggagacggc gtcgtttagg taaaagacga    660
agaagcagac gcagagaaga tccgaattac ccgaaaccga accggagcgg ttacaatttc    720
ttctttgctg agaaacattg caagctcaaa tcactttatc ccaacaagga gagagagttt    780
acgaaactta tcggagaatc gtggagcaat ctctctaccg aagaacgaat ggtaacaaat    840
tatcttttaa accgttaccg atttagtgat gaaattagat ttgtattgca gcgatttcat    900
tttagattct caaaaatatt ctcagatgtg tgggatttga gtagagttta tgttgcgttg    960
gcatgatttg aatagtatgc aagatttttg agattttgca ttcgttcatg tgtgtatgtg   1020
tgattgtagc ttgatatgat ttaacctgtt agtaaatgt gcatagacaa taagtaacat   1080
acgaagcgag tcactaagca taagagtcaa cttgttttgc tgaaaagata tcacttatga   1140
ttttcgaatc attttagctt ttttgtcact tgagcttaat gattcttctg aaattcgatt   1200
ctttgtttgg tttatgtcac attctttaga attgagaatc taagaaatgc ttacaggata   1260
tggtgaaact attcttttaa gatagcatga tgcttctttt atgattctac agtggctaag   1320 tcatttttttt tttgttctat tctttgtagc accatgg                          1357
```

<210> SEQ ID NO 19
<211> LENGTH: 34
<212> TYPE: DNA

```
<213> ORGANISM: Artificial
<220> FEATURE:
<223> OTHER INFORMATION: Primer

<400> SEQUENCE: 19
gtcttgtaca aatctaattt catcactaaa tcgg                                    34

<210> SEQ ID NO 20
<211> LENGTH: 34
<212> TYPE: DNA
<213> ORGANISM: Artificial
<220> FEATURE:
<223> OTHER INFORMATION: Primer

<400> SEQUENCE: 20
ttagatttgt acaagaccct tcctctatat aagg                                    34

<210> SEQ ID NO 21
<211> LENGTH: 19
<212> TYPE: DNA
<213> ORGANISM: Artificial
<220> FEATURE:
<223> OTHER INFORMATION: Primer

<400> SEQUENCE: 21
ttcccagtca cgacgttgt                                                     19

<210> SEQ ID NO 22
<211> LENGTH: 1006
<212> TYPE: DNA
<213> ORGANISM: Arabidopsis thaliana

<400> SEQUENCE: 22
ggatccccgg gtaccatcat aatactcatc ctccttctca aggttcgtac gtattatcaa        60
tatctagtat atacttgtct tgttctatg  ctttatatca tcattttatg acaaaaaatg       120
attaaggtct tagttaatga ttatgtatat gtgaaactta tatttagggg cacagtttaa       180
tttcgtatga taattgtcta gttagcttta tgtacttatc ataaaaacct tagtgtttat       240
cgcaatactt ttcaaatata gtgtagaatc ataatggtcc cactgtcatt atgtttgatg       300
caaatctatt tggattttgt tggataataa accgatgacg tggaccagac cagtagctat       360
aagatttggt tcacatagaa attttttata agataatgta tctaggtttg cttatgatta       420
tacatgtgat atttaataca tggcacaggt tcgtcgagtt tcacagccat aggtacaata       480
gaaggcaaat tcgattgtgg ttatctggta aaagttaagt tgggctcaga gattcttaac       540
ggcgttcttt atcattcggc ccagcccggc ccatcatcat ctccaaccgc tgttctaaac       600
aatgccgttg taccttatgt tgaaactggg aggagacggc gtcgtttagg taaaagacga       660
agaagcagac gcagagaaga tccgaattac ccgaaaccga accggagcgg ttacaatttc       720
ttctttgctg agaaacattg caagctcaaa tcactttatc ccaacaagga gagagagttt       780
acgaaactta tcggagaatc gtggagcaat ctctctaccg aagaacgaat ggtaacaaat       840
tatctttta accgttaccg atttagtgat gaaattagat ttgtacaaga cccttcctct       900
atataaggaa gttcatttca tttggagagg acacgtattt ttacaacaat taccaacaac       960
aacaaacaac aaacaacatt acaattacta tttacaatta ccatgg                    1006
```